(12) United States Patent
Nielsen

(10) Patent No.: US 12,359,187 B2
(45) Date of Patent: Jul. 15, 2025

(54) STABILIZED LIQUID ENZYME COMPOSITIONS FOR BREWING

(71) Applicant: Novozymes A/S, Bagsvaerd (DK)

(72) Inventor: Lone Kierstein Nielsen, Kgs. Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 384 days.

(21) Appl. No.: 17/774,753

(22) PCT Filed: Nov. 6, 2020

(86) PCT No.: PCT/EP2020/081228
§ 371 (c)(1),
(2) Date: May 5, 2022

(87) PCT Pub. No.: WO2021/089750
PCT Pub. Date: May 14, 2021

(65) Prior Publication Data
US 2022/0372461 A1    Nov. 24, 2022

(30) Foreign Application Priority Data
Nov. 8, 2019    (EP) ..................................... 19208025

(51) Int. Cl.
| | |
|---|---|
| *C12N 9/96* | (2006.01) |
| *C12N 9/26* | (2006.01) |
| *C12N 9/44* | (2006.01) |

(52) U.S. Cl.
CPC .............. *C12N 9/96* (2013.01); *C12N 9/2411* (2013.01); *C12N 9/2457* (2013.01); *C12Y 302/01003* (2013.01); *C12Y 302/01041* (2013.01)

(58) Field of Classification Search
None
See application file for complete search history.

(56) References Cited

U.S. PATENT DOCUMENTS

| | | | |
|---|---|---|---|
| 10,590,368 B2 * | 3/2020 | Andersen | C11D 3/046 |
| 11,827,866 B2 * | 11/2023 | Andersen | C11D 3/38663 |
| 2013/0143295 A1 | 6/2013 | Slupska et al. | |
| 2019/0100738 A1 | 4/2019 | Han | |

FOREIGN PATENT DOCUMENTS

EP    2505642 A1    11/2009

OTHER PUBLICATIONS

Back et al, 1979, Biochemistry 18(23), 5191-5196.
Chong et al, 2014, Enzyme Microb Technol 61, 55-60.
Gekko, 1982, J Biochem 91(4), 1197-1204.
Graber et al, 1989, Enzyme Microb Technol 11(10), 673-677.
Haque et al, 2005, Biophys Chem 117(1), 1-12.
Haque et al, 2006, Biophys Chem 119(3), 224-233.
Valente et al, 2006, Anal Biochem 357(1), 35-42.

* cited by examiner

Primary Examiner — Christian L Fronda
(74) Attorney, Agent, or Firm — Eric J. Fechter

(57) ABSTRACT

The invention provides liquid enzyme compositions which are physically and microbially stable. The compositions are used, for example, in beer brewing processes.

17 Claims, No Drawings
Specification includes a Sequence Listing.

STABILIZED LIQUID ENZYME COMPOSITIONS FOR BREWING

CROSS-REFERENCE TO RELATED APPLICATIONS

This application is a 35 U.S.C. 371 national application of PCT/EP2020/081228, filed Nov. 6, 2020, which claims priority or the benefit from European Patent Application No. 19208025.7, filed Nov. 8, 2019. The contents of these applications are fully incorporated herein by reference.

REFERENCE TO A SEQUENCE LISTING

This application contains a Sequence Listing in computer-readable form created on Nov. 6, 2020 as an ASCII text file, 17 kb in size, and named 15087-WO-PCT SQ listing.txt., which is incorporated herein by reference.

FIELD OF THE INVENTION

The present invention relates to liquid enzyme compositions, which are physically and microbially stable. The compositions are used, for example, in beer brewing processes.

BACKGROUND

Industrial enzymes are used in many different industries, such as household care, food, feed, and biofuels, and are supplied as both solid and liquid products. When liquid enzyme products are shipped across the world, and/or stored in warehouses, it is important that the products are sufficiently stable to maintain specifications, even when they reach the customers a long time after production. Stability includes both enzyme stability, physical stability, and microbial stability.

Microbial stability of liquid enzyme products is traditionally achieved by using preservation agents. Many different preservation agents are known, but since they act by excerting a biocidal effect, there is a desire not to use preservation agents, if possible; in particular in the food industry.

However, the choice of formulation ingredients used to develop such preservative-free and microbially stable formulations is not a simple one, because it will also affect both the enzyme stability and physical stability of the final liquid product, due to (in) compatibility issues.

SUMMARY OF THE INVENTION

The present invention provides, in a first aspect, a liquid composition, comprising
a) 0.01 to 30% w/w active enzyme protein of one or more carbohydrate degrading enzymes from EC 3.2.1.-,
b) more than 30% w/w of one or more polyols,
c) less than 10% w/w of one or more inorganic salts, and
d) a pH of less than 5;
wherein at least 40% w/w of the polyols are non-sugar polyols, and wherein the composition is substantially free of benzoates, sorbates, and sulfites.

Other aspects and embodiments of the invention are apparent from the description and examples.

Unless otherwise indicated, or if it is apparent from the context that something else is meant, all percentages are percentage by weight (% w/w).

DETAILED DESCRIPTION

We have found that it is possible to prepare preservative-free liquid enzyme products that maintains microbial stability, while not weakening the enzyme stability or the physical stability, by carefully selecting the ingredients and amounts used in the liquid enzyme composition. Thus, the liquid composition maintains microbial stability while being substantially free of commonly used preservation agents for use in foods, like benzoates, sorbates, and/or sulfites.

Microbial stability is the ability to resist microbial growth. This may be evaluated by inoculating the liquid composition with microorganisms, and measure the subsequent growth of the microorganisms to confirm that they are not proliferating.

Physical stability is the ability to maintain a transparent, preferably clear, composition. This may be evaluated by visual inspection, or by centrifugation. For example, the liquid composition may centrifugated at 1200 G for 10 minutes to determine if a pellet (solid phase) is formed. Alternatively, transparency may be measured as turbidity or haziness, by using a nephelometer to measure NTU to determine light scattering.

Enzymatic stability is the ability to maintain enzymatic activity after storage. This may be determined by measuring the enzymatic activity before and after storage (for example, 8 weeks storage at 25° C.) to determine how much activity is lost. For practical purposes, the residual activity may be determined by comparing the activity of a stored sample and a frozen reference sample, which are analyzed at the same time to eliminate analytical day-to-day variation.

The formulations of the invention were developed for use in a beer brewing process, but are generally applicable also in other processes.

Definitions

The term "malt" is understood as any malted cereal grain, in particular barley.

The term "mash" is understood as a starch containing slurry comprising crushed barley malt, crushed unmalted grain, other starch containing material, or a combination hereof, steeped in water to make wort.

The term "wort" is understood as the unfermented liquor run-off following extracting the grist during mashing.

The term "beer" is here understood as fermented wort, i.e. an alcoholic beverage brewed from barley malt, optionally adjunct and hops. The term "beer" as used herein is intended to cover at least beer prepared from mashes prepared from unmalted cereals as well as all mashes prepared from malted cereals, and all mashes prepared from a mixture of malted and unmalted cereals. The term "beer" also covers beers prepared with adjuncts, and beers with all possible alcohol contents.

Liquid Enzyme Composition

The liquid enzyme composition of the invention comprises:
a) 0.01 to 30% w/w active enzyme protein of one or more carbohydrate degrading enzymes from EC 3.2.1.-,
b) more than 30% w/w of one or more polyols,
c) less than 10% w/w of one or more inorganic salts, and
d) a pH of less than 5;
wherein at least 40% w/w of the polyols are non-sugar polyols, and wherein the composition is substantially free of benzoates, sorbates, and sulfites.

The liquid composition maintains physical stability after storage (such as 8 weeks storage at 25° C.), and in a preferred embodiment, the liquid composition is transparent. The liquid composition may be transparent if there is essentially no solid phase after centrifugation at 1200 G for 10 minutes.

As mentioned above, the liquid composition also maintains excellent enzymatic stability. The residual enzymatic activity may be at least 90% after 8 weeks storage at 25° C.

The liquid composition may be an aqueous liquid composition, comprising more than 5% w/w of water; preferably more than 10% w/w of water, more preferably more than 15% w/w of water, and most preferably more than 20% w/w of water.

Carbohydrate Degrading Enzyme

The carbohydrate degrading enzymes used in the compositions of the invention are catalytic proteins, and the term "active enzyme protein" is defined herein as the amount of catalytic protein(s), which exhibits enzymatic activity. This can be determined using an activity based analytical enzyme assay. In such assays, the enzyme typically catalyzes a reaction generating a colored compound. The amount of the colored compound can be measured and correlated to the concentration of the active enzyme protein. This technique is well-known in the art.

The carbohydrate degrading enzyme(s) are capable of degrading carbohydrates, in particular water-soluble carbohydrates. The carbohydrate degrading enzyme may be one or more enzymes selected from the group consisting of amylase, endoglucanase, xylanase, and pullulanase. In an embodiment, the carbohydrate degrading enzyme is an amylase and/or a pullulanase.

The amylase may be fungal or bacterial; e.g., an alpha-amylase (EC 3.2.1.1) from, e.g., *Bacillus*, e.g. *B. licheniformis* or *B. amyloliquefaciens*; a beta-amylase (EC 3.2.1.2) from, e.g., plant (e.g. soy bean) or from microbial sources (e.g., *Bacillus*); a fungal alpha-amylase, e.g., from *A. oryzae* or *A. niger*, a glucoamylase/amyloglucosidase (EC 3.2.1.3) from, e.g., an *Aspergillus* or *Talaromyces* species; or an isoamylase (E.C. 3.2.1.68).

The glucoamylase may have a sequence identity of at least 60%, at least 65%, at least 70%, at least 75%, at least 80%, at least 85%, at least 90%, at least 95%, at least 96%, at least 97%, at least 98%, or at least 99% to the amino acid sequence of the *Aspergillus niger* G1 or G2 glucoamylase (Boel et al. (1984), EMBO J. 3 (5), p. 1097-1102), the *A. awamori* glucoamylase disclosed in WO 84/02921, or the *A. oryzae* glucoamylase (Agric. Biol. Chem. (1991), 55 (4), p. 941-949).

The endoglucanase (E.C. 3.2.1.4) may be derived from a filamentous fungus, such as *Aspergillus, Trichoderma, Humicola*, or *Fusarium*.

The xylanase (EC 3.2.1.8 and EC 3.2.1.32) may be derived from *Aspergillus aculeatus*.

The pullulanase (EC 3.2.1.41) may be derived from *Bacillus deramificans* (see for example U.S. Pat. No. 5,736,375 or WO 2006/066579).

In a particularly preferred embodiment, the carbohydrate degrading enzyme is a glucoamylase/amyloglucosidase (EC 3.2.1.3) and/or a pullulanase (EC 3.2.1.41).

The enzyme may be a naturally occurring enzyme of bacterial or fungal origin, or it may be a variant derived from one or more naturally occurring enzymes by gene shuffling and/or by substituting, deleting or inserting one or more amino acids. Chemically modified or protein engineered mutants are included.

The liquid composition contains at least one enzyme in an amount of 0.01-30% w/w active enzyme protein; preferably in an amount of 0.05-30% w/w active enzyme protein; more preferably in an amount of 0.1-30% w/w active enzyme protein, and most preferably in an amount of 0.1-25% w/w active enzyme protein.

Polyols

The polyols (or polyhydric alcohols) as used in the liquid composition of the invention are alcohols with two or more hydroxyl groups. The polyols typically have a molecular weight lower than 500 g/mol.

Polyols include suitable sugar polyols, such as mono- and disaccharides, like glucose, fructose, galactose, sucrose, lactose, maltose, and trehalose.

Polyols also include suitable non-sugars polyols, such as glycerol, ethylene glycol, diethylene glycol, triethylene glycol, propylene glycol, dipropylene glycol, tripropylene glycol, polyethylene glycol (PEG), and sugar alcohols. The polyethylene glycol may have an average molecular weight at or below about 500. Examples of sugar alcohols are sorbitol, mannitol, erythritol, dulcitol, inositol, xylitol and adonitol.

The liquid composition contains more than 30% w/w of one or more polyols, preferably more than 35% w/w of one or more polyols, and most preferably more than 40% w/w of one or more polyols.

At least 40% w/w of the polyols are non-sugar polyols, as described above. Preferably, at least 45% w/w, or at least 50% w/w, of the polyols are non-sugar polyols.

The liquid composition may comprise more than 2% w/w of one or more sugar polyols. In an embodiment, the liquid composition comprises at least 5% w/w, preferably at least 10% w/w, of one or more sugar polyols, as described above.

Inorganic Salts

Salts are commonly used in liquid enzyme formulations; however, we have observed that when more than 10% w/w salt is used in the liquid formulation of the invention, it is detrimental to the physical stability. Thus, the liquid enzyme composition comprises less than 10% w/w of one or more inorganic salts, preferably less than 5% w/w of one or more inorganic salts.

The inorganic salts may be selected from the group consisting of Na, K, NH4, Ca, Mg, and Zn salts of mono- or divalent anions. Examples of anions include chloride, sulphate, nitrate, phosphate, formate, and acetate.

Further embodiments of the invention include:

Embodiment 1. A liquid composition, comprising
a) 0.01 to 30% w/w active enzyme protein of one or more carbohydrate degrading enzymes from EC 3.2.1.-,
b) more than 30% w/w of one or more polyols,
c) less than 10% w/w of one or more inorganic salts, and
d) a pH of less than 5;
wherein at least 40% w/w of the polyols are non-sugar polyols, and wherein the composition is substantially free of benzoates, sorbates, and sulfites.

Embodiment 2. The composition of embodiment 1, which comprises 0.05-30% w/w active enzyme protein of one or more carbohydrate degrading enzymes from EC 3.2.1.-.

Embodiment 3. The composition of embodiment 1, which comprises 0.1-30% w/w active enzyme protein of one or more carbohydrate degrading enzymes from EC 3.2.1.-.

Embodiment 4. The composition of embodiment 1, which comprises 0.5-30% w/w active enzyme protein of one or more carbohydrate degrading enzymes from EC 3.2.1.-.

Embodiment 5. The composition of embodiment 1, which comprises 0.1-25% w/w active enzyme protein of one or more carbohydrate degrading enzymes from EC 3.2.1.-.

Embodiment 6. The composition of embodiment 1, which comprises 0.5-25% w/w active enzyme protein of one or more carbohydrate degrading enzymes from EC 3.2.1.-.

Embodiment 7. The composition of any of embodiments 1-6, which comprises more than 35% w/w of polyols.

Embodiment 8. The composition of any of embodiments 1-7, which comprises at least 40% w/w of polyols.

Embodiment 9. The composition of any of embodiments 1-8, which comprises less than 5% w/w of inorganic salts.

Embodiment 10. The composition of any of embodiments 1-9, wherein the pH is less than 4.5.

Embodiment 11. The composition of any of embodiments 1-10, wherein at least 45% w/w of the polyols are non-sugar polyols.

Embodiment 12. The composition of any of embodiments 1-11, wherein at least 50% w/w of the polyols are non-sugar polyols.

Embodiment 13. The composition of any of embodiments 1-12, wherein the carbohydrate degrading enzymes are selected from the group consisting of amylase, endoglucanase, xylanase, and pullulanase.

Embodiment 14. The composition of any of embodiments 1-13, wherein the carbohydrate degrading enzymes are selected from the group consisting of amylase and pullulanase.

Embodiment 15. The composition of any of embodiments 1-14, wherein the carbohydrate degrading enzymes are selected from the group consisting of alpha-amylase, glucoamylase, and pullulanase.

Embodiment 16. The composition of any of embodiments 1-15, wherein the carbohydrate degrading enzymes are selected from the group consisting of glucoamylase and pullulanase.

Embodiment 17. The composition of any of embodiments 1-16, wherein the polyols have two or more hydroxyl groups, and a molecular weight lower than 500 g/mol.

Embodiment 18. The composition of any of embodiments 1-17, wherein the polyols are selected from the group consisting of monosaccharides, disaccharides, and non-sugar polyols.

Embodiment 19. The composition of any of embodiments 1-18, wherein the monosaccharides are selected from the group consisting of glucose, fructose, and galactose.

Embodiment 20. The composition of any of embodiments 1-19, wherein the disaccharides are selected from the group consisting of sucrose, lactose, maltose, and trehalose.

Embodiment 21. The composition of any of embodiments 1-20, wherein the non-sugar polyols are selected from the group consisting of glycerol, ethylene glycol, diethylene glycol, triethylene glycol, propylene glycol, dipropylene glycol, tripropylene glycol, polyethylene glycol (PEG), sorbitol, mannitol, erythritol, dulcitol, inositol, xylitol, and adonitol.

Embodiment 22. The composition of any of embodiments 1-21, which is transparent.

Embodiment 23. The composition of any of embodiments 1-22, wherein there is essentially no solid phase after centrifugation of the composition at 1200 G for 10 mins.

Embodiment 24. The composition of any of embodiments 1-23, which comprises more than 5% w/w of water.

Embodiment 25. The composition of any of embodiments 1-24, which comprises more than 10% w/w of water.

Embodiment 26. The composition of any of embodiments 1-25, which comprises more than 15% w/w of water.

Embodiment 27. The composition of any of embodiments 1-26, which comprises more than 20% w/w of water.

Embodiment 28. The composition of any of embodiments 1-27, which comprises more than 2% w/w of one or more sugar polyols.

Embodiment 29. The composition of any of embodiments 1-28, which comprises more than 5% w/w of one or more sugar polyols.

Embodiment 30. The composition of any of embodiments 1-29, which comprises more than 10% w/w of one or more sugar polyols.

Embodiment 31. The composition of any of embodiments 1-30, wherein the % refractive index is higher than 45.

Embodiment 32. A method for producing a brewer's wort, comprising adding the liquid composition of any of embodiments 1-31 to a mash.

The present invention is further described by the following examples which should not be construed as limiting the scope of the invention.

EXAMPLES

Chemicals were commercial products of at least reagent grade.

Glucoamylase1 (glucan 1,4-alpha-glucosidase, EC 3.2.1.3, also referred to as amyloglucosidase) has the amino acid sequence shown in SEQ ID NO: 1.

Glucoamylase2 has the amino acid sequence shown in SEQ ID NO: 2. Pullulanase (alpha-dextrin endo-1,6-alpha-glucosidase, EC 3.2.1.41) has the amino acid sequence shown in SEQ ID NO: 3.

Glucoamylase activity is measured as specified in the analytical method "AGU, Amyloglucosidase determination" from Novozymes. Briefly, amyloglucosidase hydrolyzes maltose to form α-D-glucose. After incubation, the reaction is stopped with NaOH. Glucose is phosphorylated by ATP in a reaction catalyzed by hexokinase. The glucose-6-phosphate which is formed is oxidized to 6-phosphogluconate by glucose-6-phosphate dehydrogenase. In this same reaction, an equimolar amount of NAD+ is reduced to NADH with a resultant increase in absorbance at 340 nm.

Pullulanase activity is measured as specified in the analytical method "PUN(J), Pullulanase determination" from Novozymes. Briefly, pullulanase cleaves the substrate 4,6-O-benzylidene-4-nitrophenyl-6-α-D-maltotriosyl-maltotriose. α-glucosidase removes glucose units from the non-reducing end of the formed 4-nitrophenyl-β-maltotrioside, and β-glucosidase releases 4-nitrophenyl, which—after a pH change from pH 5.0 to a basic pH >9.0—can be monitored at 405 nm in a Konelab analyzer.

% Refractive Index is measured using an ATAGO PAL-alpha pocket refractometer. % RI is the corresponding % sucrose concentration (Brix).

Example 1

Stable Liquid Glucoamylase Composition

A liquid glucoamylase (amyloglucosidase) formulation, with the composition and characteristics as shown in Table 1, was prepared and tested for physical stability, enzymatic stability, and microbial stability, as shown in Tables 2-5.

TABLE 1

| Liquid enzyme formulation. | |
|---|---|
| Parameter | Value |
| Glucoamylase1 amount | 20% w/w active enzyme protein |
| Glycerol | 50% w/w |
| pH | 4.3 |
| % Refractive Index | 58 |
| Visual appearance (t = 0) | Clear |

TABLE 2

Physical stability of the liquid enzyme formulation after incubation.

| Physical stability | Visual inspection |
|---|---|
| 4 weeks at 10° C. | Clear |
| 4 weeks at 25° C. | Clear |
| 13 weeks at 10° C. | Clear |
| 13 weeks at 25° C. | Clear |

TABLE 3

Residual enzymatic activitiy after incubation for 4 and 13 weeks.

| Incubation temperature | 4 weeks | 13 weeks |
|---|---|---|
| −18° C. | 100% | 100% |
| 10° C. | 100% | 101% |
| 25° C. | 100% | 98% |
| 40° C. | 99% | 95% |

Microbial Stability

The formulation was shown to be microbially robust towards bacteria, lactobacilli as well as yeast and mold. This was done by spiking/challenging the formulation with the microorganisms in Table 4. Each of the three bottles were inoculated to a total of $1\times10^5$ CFU/ml of the test microorganisms.

TABLE 4

Test microorganisms used in bottles 1-3.

| Bottle | Test organism |
|---|---|
| 1 | Escherichia coli |
|  | Pseudomonas aeruginosa |
|  | Salmonella havana |
|  | Acinetobacter spp. |
|  | Staphylococcus aureus |
|  | Staphylococcus xylosus |
|  | Enterococcus faecium |
| 2 | Lactobacillus buchneri |
|  | Lactobacillus para paracasei |
| 3 | Aspergillus niger |
|  | Candida parapsilosis |
|  | Candida famata |

The bottles were analyzed for CFU/ml before inoculation (blind) and after 1, 2, 3, and 5 weeks of incubation at 20-25° C. CFU (colony forming units) per ml was measured using standard microbiological methods.

TABLE 5

Microbial stability of the liquid enzyme formulation, measured as CFU/ml.

| Bottle | Blind | Added | 1 week | 2 weeks | 3 weeks | 5 weeks |
|---|---|---|---|---|---|---|
| 1 | $1.0 \times 10^2$ | $1.0 \times 10^5$ | $2.4 \times 10^3$ | $1.0 \times 10^2$ | $1.0 \times 10^2$ | $1.0 \times 10^2$ |
| 2 | $1.0 \times 10^2$ | $1.0 \times 10^5$ | $1.0 \times 10^2$ | $1.0 \times 10^2$ | $1.0 \times 10^2$ | $1.0 \times 10^2$ |
| 3 | $1.0 \times 10^2$ | $1.0 \times 10^5$ | $2.0 \times 10^4$ | $3.5 \times 10^3$ | $5.0 \times 10^3$ | $1.1 \times 10^3$ |

The data in Tables 2 and 3 show that the liquid enzyme composition of Table 1 maintains physical and enzymatic stability even after incubation for up to 13 weeks at 25° C.

The data in Table 5 show that the liquid enzyme composition of Table 1 is microbially robust towards all microorganisms in bottles 1, 2 and 3 based on a success criterea of >1 log reduction of all added test microorganisms in bottles 1, 2 and 3 after incubation for less than 4 weeks.

Example 2

Stable Liquid Glucoamylase/Pullulanase Composition

A liquid glucoamylase/pullulanase formulation, with the composition and characteristics as shown in Table 6, was prepared and tested for physical stability, enzymatic stability, and microbial stability, as shown in Tables 7-9.

TABLE 6

Liquid enzyme formulation.

| Parameter | Value |
|---|---|
| Glucoamylase2 amount | 25% w/w active enzyme protein |
| Pullulanase amount | 0.3% w/w active enzyme protein |
| Glycerol | 20% w/w |
| Glucose | 20% w/w |
| pH | 4.0 |
| % Refractive Index | >50 |
| Visual appearance (t = 0) | Clear |

TABLE 7

Physical stability of the liquid enzyme formulation after incubation.

| Physical stability | Visual inspection |
|---|---|
| 8 weeks at 10° C. | Clear |
| 8 weeks at 25° C. | Transparent |

TABLE 8

Residual enzymatic activitiy after incubation for 8 weeks.

| | Residual activity after 8 weeks | |
|---|---|---|
| Incubation temperature | Glucoamylase | Pullulanase |
| −18° C. | 100% | 100% |
| 25° C. | 96% | 99% |

Microbial Stability

The formulation was shown to be microbially robust towards bacteria, lactobacilli as well as yeast and mold. This was done by spiking/challenging the formulation with the microorganisms in Table 4 of Example 1. Each of the three bottles were inoculated to a total of $1\times10^5$ CFU/ml of the test microorganisms.

The bottles were analyzed for CFU/ml before inoculation (blind) and after 1, 2, 3, and 4 weeks of incubation at 20-25° C. CFU (colony forming units) per ml was measured using standard microbiological methods.

TABLE 9

Microbial stability of the liquid enzyme formulation, measured as CFU/ml.

| Bottle | Blind | Added | 1 week | 2 weeks | 3 weeks | 4 weeks |
|---|---|---|---|---|---|---|
| 1 | $8.0 \times 10^2$ | $1.0 \times 10^5$ | $1.0 \times 10^2$ | $1.0 \times 10^2$ | $1.0 \times 10^2$ | $4.0 \times 10^2$ |
| 2 | $1.0 \times 10^2$ | $1.0 \times 10^5$ | $1.0 \times 10^2$ | $1.0 \times 10^2$ | $1.0 \times 10^2$ | $1.0 \times 10^2$ |
| 3 | $1.1 \times 10^3$ | $1.0 \times 10^5$ | $1.0 \times 10^2$ | $1.0 \times 10^2$ | $1.0 \times 10^2$ | $1.1 \times 10^3$ |

The data in Tables 7 and 8 show that the liquid enzyme composition of Table 6 maintains physical and enzymatic stability even after incubation for 8 weeks at 25° C.

The data in Table 9 show that the liquid enzyme composition of Table 6 is microbially robust towards all microorganisms in bottles 1, 2 and 3 based on a success criterea of >1 log reduction of all added test microorganisms in bottles 1, 2 and 3 after incubation for less than 4 weeks.

---

The invention claimed is:
1. A liquid enzyme composition, comprising:
 a) 0.01 to 30% w/w active enzyme protein of glucoamylase,
 b) more than 30% w/w of one or more polyols,
 c) less than 10% w/w of one or more inorganic salts, and
 d) a pH of less than 5;
 wherein at least 40% w/w of the polyols are non-sugar polyols, and wherein the composition is substantially free of benzoates, sorbates, and sulfites.

2. The composition of claim 1, which is transparent.

3. The composition of claim 1, wherein there is essentially no solid phase after centrifugation of the composition at 1200 G for 10 mins.

4. The composition of claim 1, which further comprises a pullulanase.

5. The composition of claim 1, wherein the polyols have two or more hydroxyl groups, and a molecular weight lower than 500 g/mol.

6. The composition of claim 1, wherein the polyols are selected from the group consisting of monosaccharides, disaccharides, and non-sugar polyols.

7. The composition of claim 1, wherein the non-sugar polyols are selected from the group consisting of glycerol, ethylene glycol, diethylene glycol, triethylene glycol, propylene glycol, dipropylene glycol, tripropylene glycol, polyethylene glycol (PEG), sorbitol, mannitol, erythritol, dulcitol, inositol, xylitol, and adonitol.

8. The composition of claim 1, wherein the inorganic salt(s) are selected from the group consisting of Na, K, $NH_4$, Ca, Mg, and Zn salts of mono- or divalent anions.

9. The composition of claim 1, wherein the mono- or divalent anions are selected from the group consisting of chloride, sulphate, nitrate, phosphate, formate, and acetate.

10. The composition of claim 1, which comprises more than 35% w/w of one or more polyols.

11. The composition of claim 1, which comprises less than 5% w/w of one or more inorganic salts.

12. The composition of claim 1, which comprises a pH of less than 4.5.

13. The composition of claim 1, which comprises at least 10% w/w of water.

14. The composition of claim 1, which comprises more than 2% w/w of one or more sugar polyols.

15. A method for producing a brewer's wort, the method comprising adding the liquid composition of claim 1 to a mash.

16. The composition of claim 1, which comprises at least 20% w/w of water.

17. The composition of claim 1, which comprises more than 5% w/w of one or more sugar polyols.

* * * * *

SEQUENCE LISTING

<160> NUMBER OF SEQ ID NOS: 3

<210> SEQ ID NO 1
<211> LENGTH: 622
<212> TYPE: PRT
<213> ORGANISM: Aspergillus niger

<400> SEQUENCE: 1

```
Asn Val Ile Ser Lys Arg Ala Thr Leu Asp Ser Trp Leu Ser Asn Glu
1               5                   10                  15

Ala Thr Val Ala Arg Thr Ala Ile Leu Asn Asn Ile Gly Ala Asp Gly
            20                  25                  30

Ala Trp Val Ser Gly Ala Asp Ser Gly Ile Val Val Ala Ser Pro Ser
        35                  40                  45

Thr Asp Asn Pro Asp Tyr Phe Tyr Thr Trp Thr Arg Asp Ser Gly Leu
    50                  55                  60

Val Leu Lys Thr Leu Val Asp Leu Phe Arg Asn Gly Asp Thr Ser Leu
65                  70                  75                  80

Leu Ser Thr Ile Glu Asn Tyr Ile Ser Ala Gln Ala Ile Val Gln Gly
                85                  90                  95

Ile Ser Asn Pro Ser Gly Asp Leu Ser Ser Gly Ala Gly Leu Gly Glu
            100                 105                 110

Pro Lys Phe Asn Val Asp Glu Thr Ala Tyr Thr Gly Ser Trp Gly Arg
        115                 120                 125

Pro Gln Arg Asp Gly Pro Ala Leu Arg Ala Thr Ala Met Ile Gly Phe
    130                 135                 140

Gly Gln Trp Leu Leu Asp Asn Gly Tyr Thr Ser Thr Ala Thr Asp Ile
145                 150                 155                 160

Val Trp Pro Leu Val Arg Asn Asp Leu Ser Tyr Val Ala Gln Tyr Trp
                165                 170                 175

Asn Gln Thr Gly Tyr Asp Leu Trp Glu Glu Val Asn Gly Ser Ser Phe
            180                 185                 190

Phe Thr Ile Ala Val Gln His Arg Ala Leu Val Glu Gly Ser Ala Phe
        195                 200                 205

Ala Thr Ala Val Gly Ser Ser Cys Ser Trp Cys Asp Ser Gln Ala Pro
    210                 215                 220

Glu Ile Leu Cys Tyr Leu Gln Ser Phe Trp Thr Gly Ser Phe Ile Leu
225                 230                 235                 240

Ala Asn Phe Asp Ser Ser Arg Ser Gly Lys Asp Ala Asn Thr Leu Leu
```

```
                245                 250                 255
Gly Ser Ile His Thr Phe Asp Pro Glu Ala Ala Cys Asp Asp Ser Thr
            260                 265                 270
Phe Gln Pro Cys Ser Pro Arg Ala Leu Ala Asn His Lys Glu Val Val
        275                 280                 285
Asp Ser Phe Arg Ser Ile Tyr Thr Leu Asn Asp Gly Leu Ser Asp Ser
    290                 295                 300
Glu Ala Val Ala Val Gly Arg Tyr Pro Glu Asp Thr Tyr Tyr Asn Gly
305                 310                 315                 320
Asn Pro Trp Phe Leu Cys Thr Leu Ala Ala Glu Gln Leu Tyr Asp
                325                 330                 335
Ala Leu Tyr Gln Trp Asp Lys Gln Gly Ser Leu Glu Val Thr Asp Val
            340                 345                 350
Ser Leu Asp Phe Phe Lys Ala Leu Tyr Ser Asp Ala Ala Thr Gly Thr
        355                 360                 365
Tyr Ser Ser Ser Ser Ser Thr Tyr Ser Ser Ile Val Asp Ala Val Lys
    370                 375                 380
Thr Phe Ala Asp Gly Phe Val Ser Ile Val Glu Thr His Ala Ala Ser
385                 390                 395                 400
Asn Gly Ser Met Ser Glu Gln Tyr Asp Lys Ser Asp Gly Glu Gln Leu
                405                 410                 415
Ser Ala Arg Asp Leu Thr Trp Ser Tyr Ala Ala Leu Leu Thr Ala Asn
            420                 425                 430
Asn Arg Arg Asn Ser Val Val Pro Ala Ser Trp Gly Glu Thr Ser Ala
        435                 440                 445
Ser Ser Val Pro Gly Thr Cys Ala Ala Thr Ser Ala Ile Gly Thr Tyr
    450                 455                 460
Ser Ser Val Thr Val Thr Ser Trp Pro Ser Ile Val Ala Thr Gly Gly
465                 470                 475                 480
Thr Thr Thr Thr Ala Thr Pro Thr Gly Ser Gly Ser Val Thr Ser Thr
                485                 490                 495
Ser Lys Thr Thr Ala Thr Ala Ser Lys Thr Ser Thr Ser Thr Ser Ser
            500                 505                 510
Thr Ser Cys Thr Thr Pro Thr Ala Val Ala Val Thr Phe Asp Leu Thr
        515                 520                 525
Ala Thr Thr Thr Tyr Gly Glu Asn Ile Tyr Leu Val Gly Ser Ile Ser
    530                 535                 540
Gln Leu Gly Asp Trp Glu Thr Ser Asp Gly Ile Ala Leu Ser Ala Asp
545                 550                 555                 560
Lys Tyr Thr Ser Ser Asp Pro Leu Trp Tyr Val Thr Val Thr Leu Pro
                565                 570                 575
Ala Gly Glu Ser Phe Glu Tyr Lys Phe Ile Arg Ile Glu Ser Asp Asp
            580                 585                 590
Ser Val Glu Trp Glu Ser Asp Pro Asn Arg Glu Tyr Thr Val Pro Gln
        595                 600                 605
Ala Cys Gly Thr Ser Thr Ala Thr Val Thr Asp Thr Trp Arg
    610                 615                 620

<210> SEQ ID NO 2
<211> LENGTH: 591
<212> TYPE: PRT
<213> ORGANISM: Talaromyces emersonii

<400> SEQUENCE: 2
```

```
Ala Thr Gly Ser Leu Asp Ser Phe Leu Ala Thr Glu Thr Pro Ile Ala
1               5                   10                  15

Leu Gln Gly Val Leu Asn Asn Ile Gly Pro Asn Gly Ala Asp Val Ala
            20                  25                  30

Gly Ala Ser Ala Gly Ile Val Val Ala Ser Pro Ser Arg Ser Asp Pro
            35                  40                  45

Asn Tyr Phe Tyr Ser Trp Thr Arg Asp Ala Ala Leu Thr Ala Lys Tyr
50                      55                  60

Leu Val Asp Ala Phe Ile Ala Gly Asn Lys Asp Leu Glu Gln Thr Ile
65                      70                  75                  80

Gln Gln Tyr Ile Ser Ala Gln Ala Lys Val Gln Thr Ile Ser Asn Pro
                    85                  90                  95

Ser Gly Asp Leu Ser Thr Gly Gly Leu Gly Glu Pro Lys Phe Asn Val
                100                 105                 110

Asn Glu Thr Ala Phe Thr Gly Pro Trp Gly Arg Pro Gln Arg Asp Gly
            115                 120                 125

Pro Ala Leu Arg Ala Thr Ala Leu Ile Ala Tyr Ala Asn Tyr Leu Ile
            130                 135                 140

Asp Asn Gly Glu Ala Ser Thr Ala Asp Glu Ile Ile Trp Pro Ile Val
145                 150                 155                 160

Gln Asn Asp Leu Ser Tyr Ile Thr Gln Tyr Trp Asn Ser Ser Thr Phe
                165                 170                 175

Asp Leu Trp Glu Glu Val Glu Gly Ser Ser Phe Phe Thr Thr Ala Val
                180                 185                 190

Gln His Arg Ala Leu Val Glu Gly Asn Ala Leu Ala Thr Arg Leu Asn
            195                 200                 205

His Thr Cys Ser Asn Cys Val Ser Gln Ala Pro Gln Val Leu Cys Phe
            210                 215                 220

Leu Gln Ser Tyr Trp Thr Gly Ser Tyr Val Leu Ala Asn Phe Gly Gly
225                 230                 235                 240

Ser Gly Arg Ser Gly Lys Asp Val Asn Ser Ile Leu Gly Ser Ile His
                245                 250                 255

Thr Phe Asp Pro Ala Gly Gly Cys Asp Asp Ser Thr Phe Gln Pro Cys
                260                 265                 270

Ser Ala Arg Ala Leu Ala Asn His Lys Val Val Thr Asp Ser Phe Arg
            275                 280                 285

Ser Ile Tyr Ala Ile Asn Ser Gly Ile Ala Glu Gly Ser Ala Val Ala
            290                 295                 300

Val Gly Arg Tyr Pro Glu Asp Val Tyr Gln Gly Gly Asn Pro Trp Tyr
305                 310                 315                 320

Leu Ala Thr Ala Ala Ala Glu Gln Leu Tyr Asp Ala Ile Tyr Gln
                325                 330                 335

Trp Lys Lys Ile Gly Ser Ile Ser Ile Thr Asp Val Ser Leu Pro Phe
                340                 345                 350

Phe Gln Asp Ile Tyr Pro Ser Ala Ala Val Gly Thr Tyr Asn Ser Gly
            355                 360                 365

Ser Thr Thr Phe Asn Asp Ile Ile Ser Ala Val Gln Thr Tyr Gly Asp
    370                 375                 380

Gly Tyr Leu Ser Ile Val Glu Lys Tyr Thr Pro Ser Asp Gly Ser Leu
385                 390                 395                 400

Thr Glu Gln Phe Ser Arg Thr Asp Gly Thr Pro Leu Ser Ala Ser Ala
                405                 410                 415

Leu Thr Trp Ser Tyr Ala Ser Leu Leu Thr Ala Ser Ala Arg Arg Gln
```

```
                420            425            430
Ser Val Val Pro Ala Ser Trp Gly Glu Ser Ala Ser Ser Val Pro
            435                440            445

Ala Val Cys Ser Ala Thr Ser Ala Thr Gly Pro Tyr Ser Thr Ala Thr
450                455                460

Asn Thr Val Trp Pro Ser Ser Gly Ser Gly Ser Ser Thr Thr Thr Ser
465                470                475                480

Ser Ala Pro Cys Thr Thr Pro Thr Ser Val Ala Val Thr Phe Asp Glu
            485                490                495

Ile Val Ser Thr Ser Tyr Gly Glu Thr Ile Tyr Leu Ala Gly Ser Ile
            500                505                510

Pro Glu Leu Gly Asn Trp Ser Thr Ala Ser Ala Ile Pro Leu Arg Ala
            515                520            525

Asp Ala Tyr Thr Asn Ser Asn Pro Leu Trp Tyr Val Thr Val Asn Leu
530                535                540

Pro Pro Gly Thr Ser Phe Glu Tyr Lys Phe Phe Lys Asn Gln Thr Asp
545                550                555                560

Gly Thr Ile Val Trp Glu Asp Pro Asn Arg Ser Tyr Thr Val Pro
            565                570            575

Ala Tyr Cys Gly Gln Thr Thr Ala Ile Leu Asp Asp Ser Trp Gln
            580                585            590

<210> SEQ ID NO 3
<211> LENGTH: 828
<212> TYPE: PRT
<213> ORGANISM: Artificial
<220> FEATURE:
<223> OTHER INFORMATION: Pullulanase derived from Bacillus deramificans

<400> SEQUENCE: 3

Asp Ser Thr Ser Thr Glu Val Ile Val His Tyr His Arg Phe Asp Ser
1               5                   10                  15

Asn Tyr Ala Asn Trp Asp Leu Trp Met Trp Pro Tyr Gln Pro Val Asn
            20                  25                  30

Gly Asn Gly Ala Ala Tyr Glu Phe Ser Gly Lys Asp Asp Phe Gly Val
        35                  40                  45

Lys Ala Asp Val Gln Val Pro Gly Asp Asp Thr Gln Val Gly Leu Ile
50                  55                  60

Val Arg Thr Asn Asp Trp Ser Gln Lys Asn Thr Ser Asp Asp Leu His
65                  70                  75                  80

Ile Asp Leu Thr Lys Gly His Glu Ile Trp Ile Val Gln Gly Asp Pro
                85                  90                  95

Asn Ile Tyr Tyr Asn Leu Ser Asp Ala Gln Ala Ala Thr Pro Lys
            100                 105                 110

Val Ser Asn Ala Tyr Leu Asp Asn Glu Lys Thr Val Leu Ala Lys Leu
        115                 120                 125

Thr Asn Pro Met Thr Leu Ser Asp Gly Ser Ser Gly Phe Thr Val Thr
130                 135                 140

Asp Lys Thr Thr Gly Glu Gln Ile Pro Val Thr Ala Ala Thr Asn Ala
145                 150                 155                 160

Asn Ser Ala Ser Ser Ser Glu Gln Thr Asp Leu Val Gln Leu Thr Leu
                165                 170                 175

Ala Ser Ala Pro Asp Val Ser His Thr Ile Gln Val Gly Ala Ala Gly
            180                 185                 190

Tyr Glu Ala Val Asn Leu Ile Pro Arg Asn Val Leu Asp Ser Ser Gln
```

```
                195                 200                 205
Tyr Tyr Tyr Ser Gly Asp Asp Leu Gly Asn Thr Tyr Thr His Lys Ala
    210                 215                 220
Thr Thr Phe Lys Val Trp Ala Pro Thr Ser Thr Gln Val Asn Val Leu
225                 230                 235                 240
Leu Tyr Asn Ser Ala Thr Gly Ser Val Thr Lys Thr Val Pro Met Thr
                245                 250                 255
Ala Ser Gly His Gly Val Trp Glu Ala Thr Val Asn Gln Asn Leu Glu
            260                 265                 270
Asn Trp Tyr Tyr Met Tyr Glu Val Thr Gly Gln Gly Ser Thr Arg Thr
        275                 280                 285
Ala Val Asp Pro Tyr Ala Thr Ala Ile Ala Pro Asn Gly Thr Arg Gly
    290                 295                 300
Met Ile Val Asp Leu Ala Lys Thr Asp Pro Ala Gly Trp Asn Ser Asp
305                 310                 315                 320
Lys His Ile Thr Pro Lys Asn Ile Glu Asp Glu Val Ile Tyr Glu Met
                325                 330                 335
Asp Val Arg Asp Phe Ser Ile Asp Pro Asn Ser Gly Met Lys Asn Lys
            340                 345                 350
Gly Lys Tyr Leu Ala Leu Thr Glu Lys Gly Thr Lys Gly Pro Asp Gly
        355                 360                 365
Val Lys Thr Gly Ile Asp Ser Leu Lys Gln Leu Gly Ile Thr His Val
    370                 375                 380
Gln Leu Met Pro Val Phe Ala Phe Ala Ser Val Asp Glu Thr Asp Pro
385                 390                 395                 400
Thr Gln Asp Asn Trp Gly Tyr Asp Pro Arg Asn Tyr Asp Val Pro Glu
                405                 410                 415
Gly Gln Tyr Ala Thr Asn Ala Asn Gly Thr Ala Arg Ile Lys Glu Phe
            420                 425                 430
Lys Glu Met Val Leu Ser Leu His Arg Glu His Ile Gly Val Asn Met
        435                 440                 445
Asp Val Val Tyr Asn His Thr Phe Ala Thr Gln Ile Ser Asp Phe Asp
    450                 455                 460
Lys Ile Val Pro Glu Tyr Tyr Tyr Arg Thr Asp Asp Ala Gly Asn Tyr
465                 470                 475                 480
Thr Asn Gly Ser Gly Thr Gly Asn Glu Ile Ala Ser Glu Arg Pro Met
                485                 490                 495
Val Gln Lys Phe Ile Ile Asp Ser Leu Lys Tyr Trp Val Asn Glu Tyr
            500                 505                 510
His Ile Asp Gly Phe Arg Phe Asp Leu Met Ala Leu Leu Gly Lys Asp
        515                 520                 525
Thr Met Ser Lys Ala Ala Ser Glu Leu His Ala Ile Asn Pro Gly Ile
    530                 535                 540
Ala Leu Tyr Gly Glu Pro Trp Thr Gly Gly Thr Ser Ala Leu Pro Glu
545                 550                 555                 560
Asp Gln Leu Leu Thr Lys Gly Ala Gln Lys Gly Met Gly Val Ala Val
                565                 570                 575
Phe Asn Asp Asn Leu Arg Asn Ala Leu Asp Gly Asn Val Phe Asp Ser
            580                 585                 590
Ser Ala Gln Gly Phe Ala Thr Gly Ala Thr Gly Leu Thr Asp Ala Ile
        595                 600                 605
Lys Asn Gly Val Glu Gly Ser Ile Asn Asp Phe Thr Ser Ser Pro Gly
    610                 615                 620
```

-continued

```
Glu Thr Ile Asn Tyr Val Thr Ser His Asp Asn Tyr Thr Leu Trp Asp
625             630             635             640

Lys Ile Ala Leu Ser Asn Pro Asn Asp Ser Glu Ala Asp Arg Ile Lys
            645             650             655

Met Asp Glu Leu Ala Gln Ala Val Val Met Thr Ser Gln Gly Val Pro
            660             665             670

Phe Met Gln Gly Gly Glu Glu Met Leu Arg Thr Lys Gly Gly Asn Asp
        675             680             685

Asn Ser Tyr Asn Ala Gly Asp Thr Val Asn Glu Phe Asp Trp Ser Arg
        690             695             700

Lys Ala Gln Tyr Pro Asp Val Phe Asn Tyr Tyr Ser Gly Leu Ile His
705             710             715             720

Leu Arg Leu Asp His Pro Ala Phe Arg Met Thr Thr Ala Asn Glu Ile
                725             730             735

Asn Ser His Leu Gln Phe Leu Asn Ser Pro Glu Asn Thr Val Ala Tyr
            740             745             750

Glu Leu Thr Asp His Val Asn Lys Asp Lys Trp Gly Asn Ile Ile Val
        755             760             765

Val Tyr Asn Pro Asn Lys Thr Ala Ala Thr Ile Asn Leu Pro Ser Gly
    770             775             780

Lys Trp Ala Ile Asn Ala Thr Ser Gly Lys Val Gly Glu Ser Thr Leu
785             790             795             800

Gly Gln Ala Glu Gly Ser Val Gln Val Pro Gly Ile Ser Met Met Ile
            805             810             815

Leu His Gln Glu Val Ser Pro Asp His Gly Lys Lys
            820             825
```